(12) United States Patent
Wood

(10) Patent No.: US 6,614,215 B1
(45) Date of Patent: Sep. 2, 2003

(54) PARTICLE DETECTION SYSTEM AND COMPONENTS THEREOF

(75) Inventor: Michael Anthony Wood, Leamington Spa (GB)

(73) Assignee: Microbial Systems Limited (GB)

( * ) Notice: Subject to any disclaimer, the term of this patent is extended or adjusted under 35 U.S.C. 154(b) by 0 days.

(21) Appl. No.: 09/700,352
(22) PCT Filed: May 17, 1999
(86) PCT No.: PCT/GB99/01562
§ 371 (c)(1),
(2), (4) Date: Jan. 18, 2001
(87) PCT Pub. No.: WO99/60379
PCT Pub. Date: Nov. 25, 1999

(30) Foreign Application Priority Data

May 16, 1998 (GB) .............................................. 9810492

(51) Int. Cl.$^7$ ................................................ G01S 3/02
(52) U.S. Cl. .................................. 324/76.36; 324/76.36
(58) Field of Search ........................ 250/573; 324/71.4, 324/76.36; 356/73, 356, 339, 72

(56) References Cited

U.S. PATENT DOCUMENTS

| 4,673,288 A | 6/1987 | Thomas et al. ............... 356/72 |
|---|---|---|
| 4,790,653 A | 12/1988 | North, Jr. ..................... 356/73 |
| 4,818,103 A | 4/1989 | Thomas et al. ............... 356/72 |
| 4,927,268 A * | 5/1990 | Carr et al. .................... 356/336 |
| 4,997,275 A | 3/1991 | Gaucher et al. .............. 356/72 |
| 5,013,150 A * | 5/1991 | Watts et al. .................... 356/73 |
| 5,106,187 A * | 4/1992 | Bezanson ..................... 356/73 |
| 5,135,302 A * | 8/1992 | Hirako ......................... 356/73 |
| 5,166,537 A * | 11/1992 | Horiuchi et al. ............. 250/573 |
| RE36,074 E * | 2/1999 | Kouzuki ..................... 324/71.4 |
| 6,320,656 B1 * | 11/2001 | Ferrante et al. ............. 356/339 |

FOREIGN PATENT DOCUMENTS

| EP | 0 068 404 A1 | 1/1983 | |
|---|---|---|---|
| EP | 0 279 000 A1 | 8/1988 | |
| GB | WO 91/04507 | * 4/1991 | ........... G02B/21/00 |

* cited by examiner

Primary Examiner—N. Le
Assistant Examiner—Walter Benson
(74) Attorney, Agent, or Firm—Woodcock Washburn, LLP

(57) ABSTRACT

A combined impedance and fluorescence particle detection system including an optically transmissive plate having an orifice for the flow of particles therethrough, a light source which operably directs light on a particle at the orifice, and a light detector positioned so as to detect light which is emitted by the particle, and wherein the plate acts as a waveguide to direct light along part of its path between the light source and light detector.

32 Claims, 3 Drawing Sheets

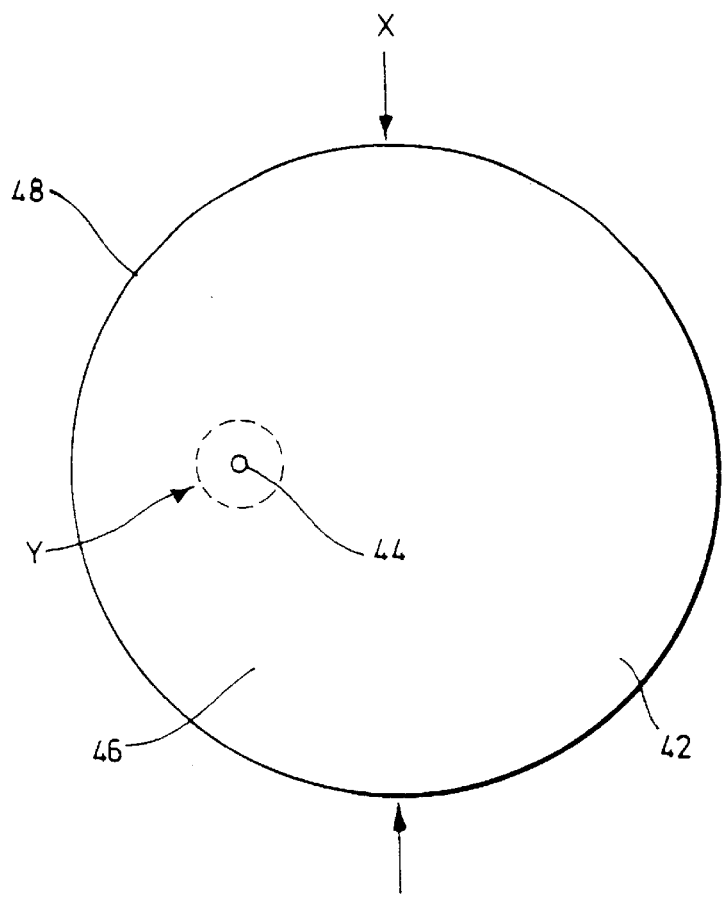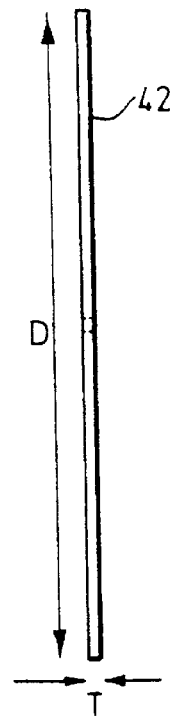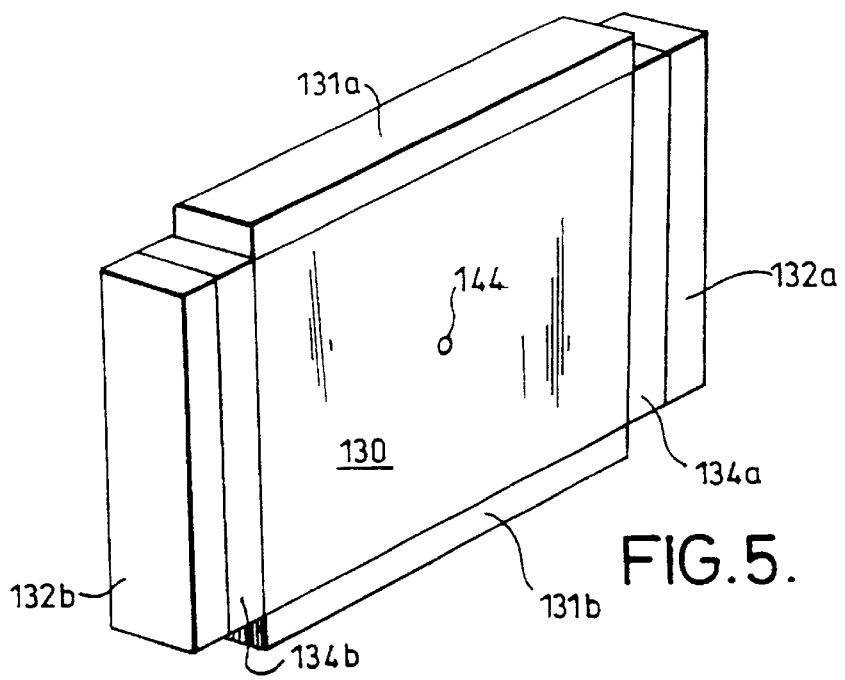

PARTICLE DETECTION SYSTEM AND COMPONENTS THEREOF

The invention relates to a particle detection system in particular such a system comprising an impedance particle detector and fluorescence detector.

It is known to detect particles such as blood cells or yeast cells for example within a sample by passing the particles through a narrow orifice and detecting variations in the impedance across the orifice. Additionally, it is known to dye or stain samples with a suitable fluorescent dye and then illuminate the particles with a suitable source of light such as laser light of a fundamental frequency and thereafter determine the nature of the particles by the fluorescence signal emitted from the particles.

However, such known systems are very complex, costly, require continuous adjustment and are limited in terms of the minimum size of particles that can be detected. Accordingly, the invention seeks to improve impedance and fluorescent particle detection systems preferably making them more economical to manufacture and/or more efficient to operate. An object is to simplify the optical system and integrate the optics with the impedance system, especially by using an orifice plate as part of the fluorescence and impedance systems.

According to one aspect of the invention there is provided a combined impedance and fluorescence particle detection system comprising an optically transmissive plate having an orifice for the flow of particles therethrough, a light source which operably directs light on a particle at the orifice, and a light detector positioned so as to detect light which is emitted by the particle, and wherein the plate acts as a waveguide to direct light along part of its path between the light source and light detector. Beneficially therefore the plate comprises an orifice to effect the impedance measurement which plate also acts as a waveguide for part of the optical system. For example light can be transmitted from the orifice to a detector via the plate and/or to the orifice via the plate from a light source.

The direction of flow of particles passes through the plate, however, at least part of the light path between the source and detector can be in different direction with respect to the particle flow direction. In one particular form, light is projected from the light source substantially in line with the particle flow direction and the light detector is substantially at right angles thereto. In another form, the source and detector are substantially in line, therefore on opposite sides of the orifice plate.

Preferably the system is operable at two or more fundamental light frequencies to observe fluorescence. The light source can comprise at least one individual unit which emits light at different frequencies. Also or alternatively, more than one light source is provided enabling use of two different wavelengths of light. Beneficially this enables different properties of the particles to be measured. Preferably a detector is provided for each light source in order to determine the fluorescence at a given wavelength.

In a preferred form, a light source and/or a light detector is optically coupled to the orifice plate. The light source and/or detector can be directly optically coupled to the orifice plate. However, preferably the light detector can be directly optically coupled to a filter which is directly optically coupled to the orifice plate. Preferably the plate comprises a substantially straight edge for attachment of or coupling of the light sources and/or light detectors. In preferred forms, the orifice plate is polygonal especially of quadrilateral, hexagonal or octagonal shape. None, one or more, indeed all, edges of the orifice plate can carry a light source or detector. The plate can also be disc shaped.

To optimise efficiency of light transfer to the detector the waveguide properties of the plate are preferably optimised. The plate surfaces such as faces and/or edges can be treated so as to increase internal reflections within the plate. For example, the faces and/or edges can be coated such as with silver or aluminium.

In a preferred form, at least part of the plate edge is so treated so as to increase reflections towards the detector. In a preferred form both faces of the plate are partially treated so as increase internal reflections.

Accordingly, fluorescent light initially scattered away from the detector can be reflected by the silvered edge back towards the detector.

Preferably, the orifice is located in a region of relatively high concentration of internally reflected light, possibly a focal point of the plate. For example, for a disc-shaped plate this can be a central position or where coated surfaces are used, an off-centre position. Combinations of the following three features are possible (to provide six possibilities): the orifice is positioned at a point of increased concentration of internal reflections within the plate, one or more edges of the plate are treated especially by coating to increase internal reflection, one or more faces of the plate are treated such as by metallic coating to increase internal reflection.

The plate for example can be a ruby, quartz or sapphire crystal, or other optically transparent medium. Preferably the refractive index of the plate is higher than saline or other media such as diluent used to carry or dilute the sample particles. Preferably, the surface finish on the plate is smooth to a quarter wavelength.

Preferably a filter is positioned between the plate and the detector in order to attenuate frequencies other than the fluorescence emission frequency from the particles. Accordingly, the filter is preferably a band pass filter wherein the optimum transmission is based on the emission frequency from the particles which is of course shifted away from the fundamental frequency of the light source and or the characteristics are chosen to maximise the difference in attenuation between the emissive frequency from the particles and the fundamental frequency of the light source.

Preferably, the optically transmissive orifice plate is made of one piece but can be made of components or parts such as a first orifice carrying part mounted in a larger mount or slide part to improve handling and positioning of the plate within the particle detection system. Such a mounting part can for example be a glass slide and preferably the first part is optically bonded to the mount part using a suitable adhesive having a refractive index similar to that of the orifice carrying part of the plate. Preferably the surfaces and/or edges of the orifice carrying part and/or the mount part are treated so as to increase internal reflections, and optimise transfer of light to the detector or from the light source.

Another aspect of the invention provides a light waveguide or an optically transmissive plate for a particle detection system which plate comprises an orifice for allowing flow of particles through the plate and part of the extremities or surfaces of the plate are treated so as to increase internal optical reflections within the plate. The plate comprises an optically transparent region adjacent or surrounding the orifice thereby to allow input and output of light to and from the plate. Additionally, at least part of the extremities of the plate are also optically transparent to enable attachment of a light source or detector to said part.

Embodiments of the invention will now be described, by way of example only, with reference to the accompanying drawings, in which:

FIGS. 3 and 4 are schematic front and side elevations of an orifice plate according to the invention in a slightly different form to that shown in FIG. 2; and FIG. 5 is a schematic perspective view of another embodiment of the invention.

Figure 1:
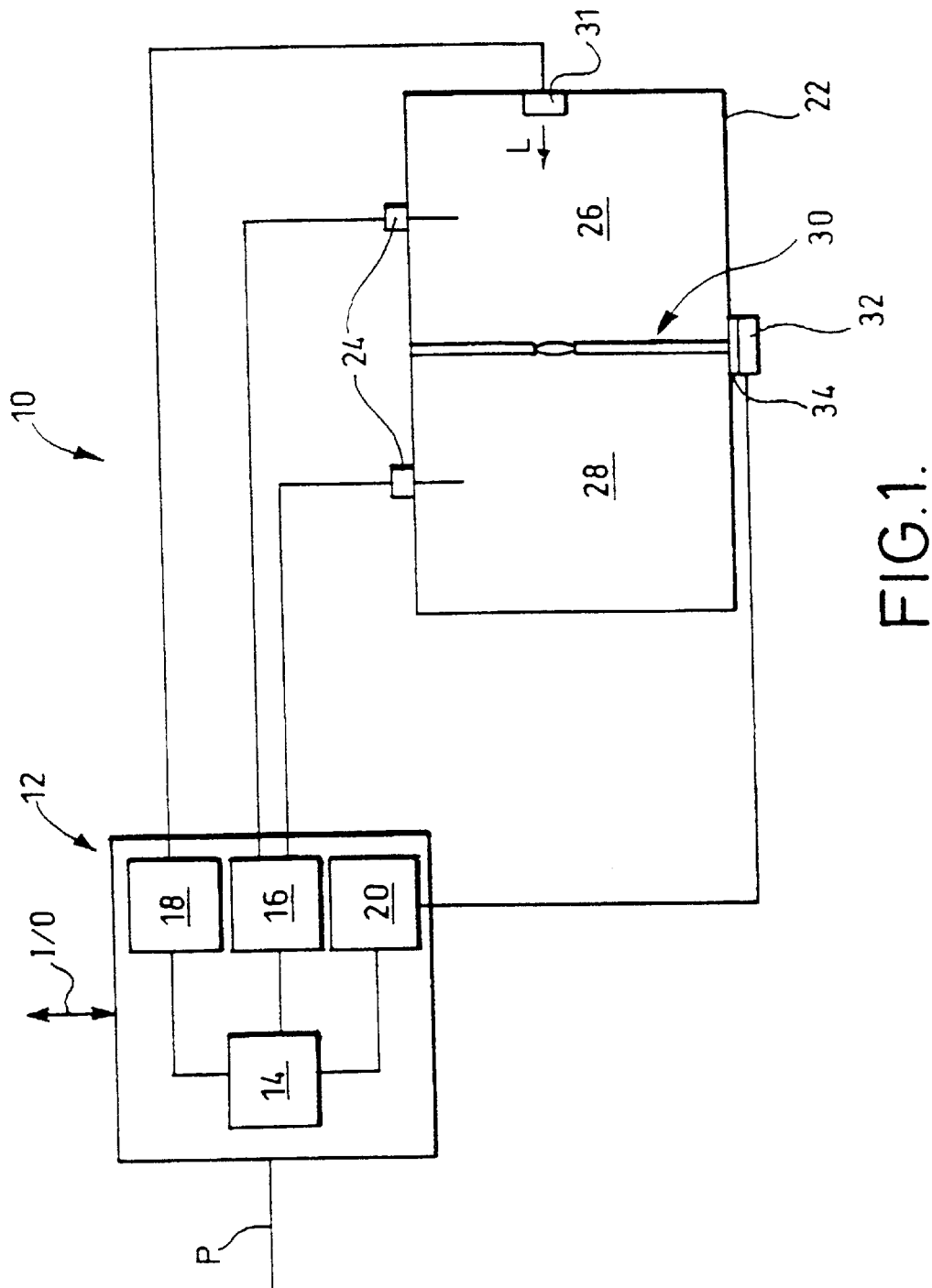
FIG. 1 is a schematic block diagram of a system according to the invention.

Referring to FIG. 1 it can be seen that a particle detection system 10 according to the invention comprises a controller 12 having a microprocessor 14 which operably communicates with an impedance detection circuit 16, laser controller 18, and light detector circuit 20. The controller 12 further comprises a power input line P and suitable means for powering each of sub-systems 14 to 20, and at least one input/output port I/O for example for communication with a display or printer.

System 10 further comprises a sample chamber 22 having a pair of electrodes 24, one disposed in each of compartments 26 and 28. The compartments 26 and 28 are separated by a plate 30 comprising an orifice 44 (see FIG. 2; the orifice 44 is not shown in FIG. 1 for clarity), which allows the flow of particles between the compartments 26 and 28. A light source such as a laser 31 is provided for directing a light beam L at the orifice 30. The light source 31 is controlled by laser controller 18 and preferably emits a coherent light beam L principally of a fundamental frequency or wavelength. For example laser 31 can be a low cost semiconductor laser. The laser 31 can have a fundamental wavelength of between say 300 and 700 nm.

System 10 further comprises a light detector 32 in optical contact with plate 30 and separated therefrom by a light filter 34. Detector 32 operably communicates with detection circuit 20.

Figure 2:
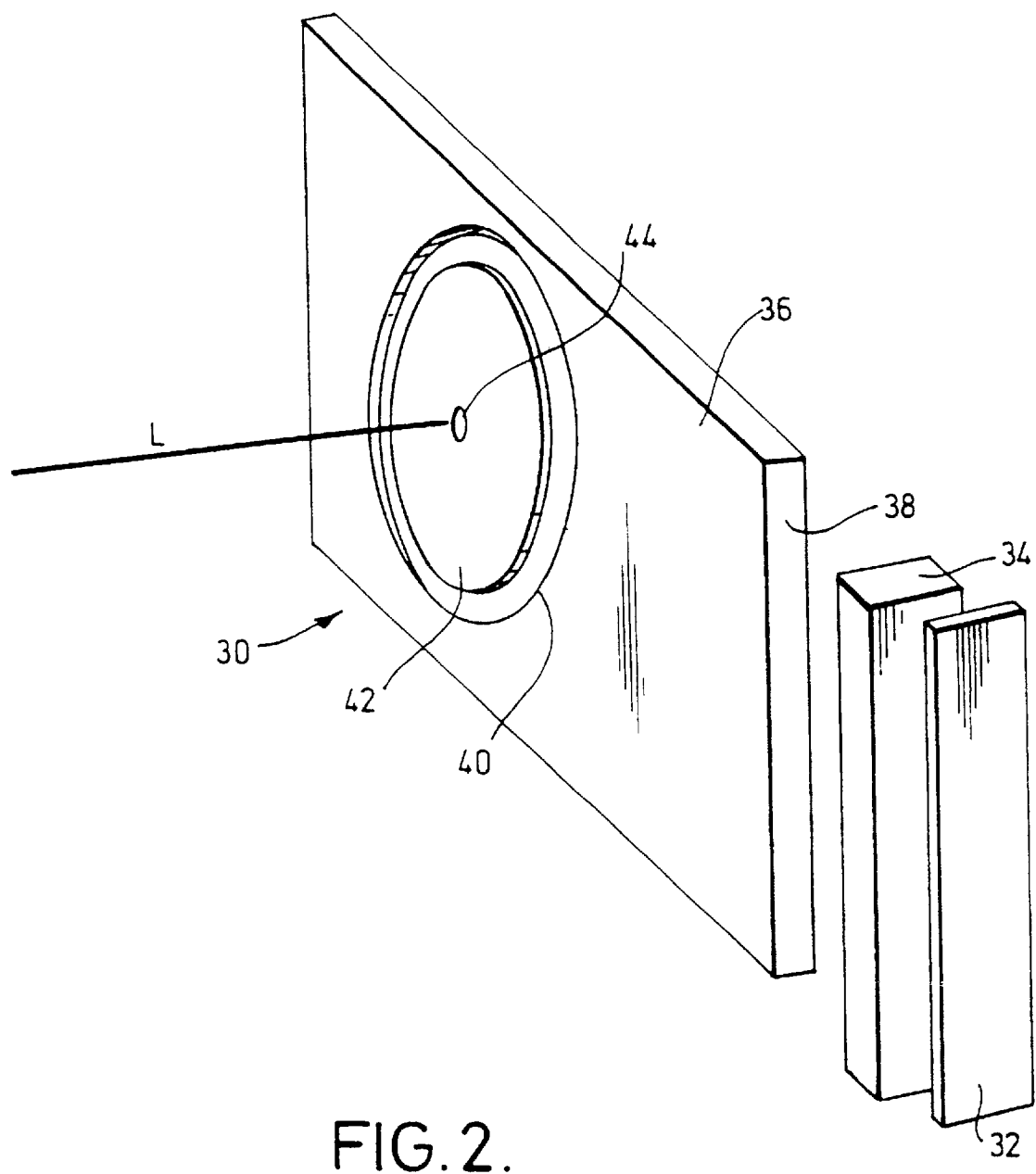
FIG. 2 is a schematic perspective view of the orifice plate assembly and part of the optical system according to the invention.

Referring to FIGS. 2 to 4, greater detail of part of the plate 30 is shown. Plate 30 is made up of a mount 36 such as a glass slide. The outer faces and edges of the glass slide 36 are preferably treated to increase internal reflections, such as by silvering. However, mount 36 comprises an untreated edge 38 which abuts filter 34 which is in optical communication with detector 32.

Mount 36 further comprises an aperture 40 for receiving a disc 42 having an orifice 44. The disc 42 is preferably optically coupled to an edge of mount 36 which defines aperture 40 for example using a suitable refractive adhesive. Accordingly plate 30 can comprise a first orifice carrying part such as disc 42 optically mounted in a second mount part 36.

Disc 42 is shown in greater detail in FIGS. 3 and 4 where it can be seen that in its preferred form disc 42 is a fairly flat disc shape, for example, having a thickness T of about 30 to 200 microns more preferably 75 to 180 microns and more preferably still 80 to 160 microns, and a diameter D in the order of 5 to 15 millimeters and more preferably 10 millimeters. Disc 42 can comprise a ruby or sapphire crystal for example.

Disc 42 further comprises front and back faces 46 and an outer edge 48. Preferably, the front and back faces are treated so as to increase internal reflections within the disc 42. An aperture or region Y surrounding orifice 44 can be left untreated. For example, the diameter of aperture Y can be in the order of a millimeter while the diameter of orifice 44 might be in the order of 30 to 80 microns. Preferably the edge 48 is treated between the positions X marked on the circumference of disc 42 so as to increase internal reflections adjacent orifice 44 thereby directing light towards light detector 32, i.e. reflecting back to the right of the page as viewed in FIG. 3.

In this example, shown in FIG. 3, where half the edge 48 of plate 42 is silvered, orifice 44 is located halfway between the centre of the circular disc and the silvered edge 48. But the orifice 44 can be centrally located as shown in FIG. 2.

In use, a sample is placed in one of compartments 26 or 28 and particles are drawn through orifice 44 into the other compartment. The size of the aperture 44 is such as to allow individual particles to flow between compartments 26 and 28. This movement of particles through orifice 44 is detected due to variation of impedance between electrodes 24 i.e. through the electrolyte within compartments 26 and 28. This is detected using circuit 16 and microprocessor 14 to count the number of particles for example and/or size the particles flowing between the compartments. Additionally, microprocessor 14 and circuit 18 are used to drive light source 31 so as to direct a light beam L at the orifice 44. By suitably dyeing or staining the particles in a sample using a fluorescent dye, the particles passing through orifice 44 emit light at a different frequency to the fundamental frequency of the light source 31. At least part of the emitted fluorescent signal is captured by disc 42 surrounding orifice 44. Disc 42 thereafter acts as a waveguide to direct the emitted light towards light detector 32. This waveguide action is assisted by the silvered faces 46 of disc 44 and the silvered edge 48.

The light transmitted by disc 42 is transferred into mount 36 and in turn to edge 38 thereafter into filter 34 and eventually on to detector 32. Beneficially since mount 36 is made of an optically transmissive material such as glass, and has silvered faces and edges, the amount of light emitted by particles at orifice 44 which reaches detector 32 is optimised.

A further embodiment of a suitable light source, light detector and orifice plate arrangement according to the invention is shown in FIG. 5. In this embodiment like features with the earlier embodiments are given the same two digit reference number as earlier prefixed with the digit 1. Accordingly, optically transmissive plate 130 comprises an aperture 144. Plate 130 is an integral plate made from optically transmissive material such as a ruby or sapphire crystal. Plate 130 in this example is rectangular wherein the edges of the plate have optically contacted therewith, for example by using an optically transmissive adhesive, an optical component of the fluorescence system. Here, a light source 131a such as a laser is attached to the upper edge of plate 142 and a suitable light detector 132a is attached via filter 134a to a side edge of plate 130. An associated light source and light detector operate respectively to project light on to particles passing through orifice 144 and detect emitted fluorescent light scattered through plate 130 via filter 134a to detector 132a Similarly, a second light source 131b is attached to the lower edge of plate 130 and an associated detector and filter 132b and 134b are attached to the other side edge of plate 142 to enable detection of fluorescent light of suitable wavelengths emitted from the particles passing through orifice 144. The front and rear faces of plate 130 can of course be treated to increase internal reflections.

Plate 130 of this example can be of a two or more part construction also. The waveguide properties of the plate are a result of the plate active co-operation in directing light between the light source and light detector due for example to total internal reflections at the surface of the plate which reflections can be enhanced by coatings. Beneficially also, the solid angle at the orifice surface defined by the edge of the plate at the orifice is optimised to allow sufficient capture of emitted light from a particle. Preferable, the surface defined in the orifice is continuous and therefore formed integrally in part of the plate.

In another form of the invention, edge 38 is directly coupled to a bundle of fibreoptic cables. That part of edge 38 not in optical contact with the end of an optical fibre is masked so as to optimise capture of light inpinging on the edge. In addition, preferably an interference filter is positioned between the optical fibres and the detector to select the fluorescent signal over any background signal for example. Beneficially, the fibreoptic cables act to collimate the light and enable transmission of the fluorescent signal to a detector somewhat remote from mount 36.

What is claimed is:

1. A combined impedance and fluorescence particle detection system comprising an optically transmissive plate having an orifice for the flow of particles therethrough, a light source which operably directs light on a particle at the orifice, and a light detector positioned so as to detect light which is emitted by the particle, and wherein the plate acts as a waveguide to direct light emitted by the particle along at least part of its path between the orifice and the light detector.

2. A system according to claim 1 wherein the light source operably projects light substantially in line with the particle flow direction and the light detector is out of line therewith and preferably substantially at right angles thereto.

3. A system according to claim 2 wherein the light is projected against the direction of flow of particles in use.

4. A system according to claim 3 wherein the plate is adapted substantially to block transmission of light from the light source to the sample other than through the orifice.

5. A system according to claim 1 wherein light is transmitted to the orifice via the plate from a light source.

6. A system according to claim 5 wherein the light source and light detector are substantially in line, on opposite sides of the orifice plate.

7. A system according to claim 1 operable at two or more different wavelengths of light.

8. A system according to claim 7 comprising at least one light emitting unit which is operable at two ore more different fundamental frequencies.

9. A system according to claim 7 comprising two or more light sources.

10. A system according to claim 7 wherein a detector is provided for each light source and/or fundamental incident frequency in order to determine the fluorescence at a given wavelength.

11. A system according to claim 1 wherein at least one of a light source and a light detector is optically coupled to the orifice plate.

12. A system according to claim 11 wherein a light source and/or detector is directly optically coupled to the orifice plate.

13. A system according to claim 1 wherein the light detector is directly optically coupled to a filter which is directly optically coupled to the orifice plate.

14. A system according to claim 1 wherein the orifice plate comprises a substantially straight edge for at least one of the light sources and the light detectors.

15. A system according to claim 1 wherein the orifice plate is polygonally shaped.

16. A system according to claim 15 wherein one or more edges of the orifice plate carries at least one of a light source and a light detector.

17. A system according to claim 1 wherein the waveguide properties of the orifice plate are enhanced by treating part of the orifice plate surfaces to increase internal reflections.

18. A system according to claim 17 wherein the treated surface comprises a reflective coating such as a metallic coat.

19. A system according to claim 17 wherein at least part of the orifice plate edge is so treated so as to increase reflections.

20. A system according to claim 17 wherein the faces of the plate are partially treated so as to increase internal reflections.

21. A system according to claim 1 wherein the orifice is located in a region of the plate of relatively high concentration of internally reflected light.

22. A system according to claim 1 having an orifice plate wherein at least one of the orifices is positioned at a point of increased concentration of internal reflections within the plate, one or more edges of the plate are treated especially by coating to increase internal reflection, and one or more faces of the plate are treated such as by metallic coating to increase internal reflection.

23. A system according to claim 1 wherein the orifice plate has a refractive index higher than saline or any other media such a diluent used to carry or dilute the sample particles which media operably surrounds the orifice.

24. A system according to claim 1 wherein a filter is positioned between the plate and the detector in order to attenuate frequencies other than the fluorescence emission frequency from the particles.

25. A system according to claim 24 wherein the filter is a band pass filter wherein the characteristics are chosen to maximise the difference of attenuation between the emissive frequency from the particles and the fundamental frequency of the light source.

26. A system according to claim 1 wherein the optically transmissive orifice plate is an integral one piece construction.

27. A system according to claim 1 wherein the orifice plate comprises a first orifice carrying part mounted in a second mount part.

28. A system according to claim 27 wherein the first part is optically bonded to the second part using a suitable adhesive having a refractive index similar to that of the first part of the plate.

29. A system according to claim 1 comprising an optical fibre between the plate and detector.

30. An optically transmissive plate for a particle detection system which plate comprises an orifice for allowing flow of particles through the plate and part of the extremities or surfaces of the plate are treated so as to increase internal optical reflections within the plate.

31. An optically transmissive plate for a particle detection system, the plate comprising an orifice for allowing a flow of particles through the plate and wherein part of the extremities or surfaces of the plate are treated so as to increase internal optical reflections within the plate and to enable the plate to act as a waveguide to direct light emitted by the flow of particles along at least part of its path between the orifice and an external surface of the plate.

32. A combined impedance and fluorescence particle detection system comprising a plate having an orifice for the flow of particles therethrough and comprising an optically transmissive material, a light source which operably directs light on a particle at the orifice, and a light detector positioned so as to detect light which is emitted by the particle, orifice, and a light detector positioned so as to detect light which is emitted by the particle, and wherein the plate acts as a waveguide to direct light emitted by the flow of particles along at least part of its path between the orifice and light detector through the optically transmissive material.

* * * * *

UNITED STATES PATENT AND TRADEMARK OFFICE
CERTIFICATE OF CORRECTION

PATENT NO.     : 6,614,215 B1
DATED          : September 2, 2004
INVENTOR(S)    : Michael Anthony Wood It is certified that error appears in the above-identified patent and that said Letters Patent is hereby corrected as shown below:

Column 2,
Line 8, insert -- to -- after "as";

Column 4,
Line 51, delete "Preferable," and insert -- Preferably -- therefor;

Column 5,
Line 23, delete "ore" and insert -- or -- therefor;
Line 33, insert -- at least one of -- after "wherein";
Line 34, delete "and/or" and insert -- and a light -- therefor;

Column 6,
Line 12, delete "a" and insert -- as -- therefor;
Lines 34-38, delete "An optionally transmissive plate for a particle detection system which plate comprises an orifice for allowing flow of particles through the plate and part of the extremities or surfaces of the plate are treated so as to increase internal optical reflections within the plate." and insert --A system according to claim 29 wherein two or more optical fibres operably direct light through an interference filter which light in turn is then transmitted into the detector.-- therefor.

Signed and Sealed this

Twenty-third Day of November, 2004

JON W. DUDAS
*Director of the United States Patent and Trademark Office*